United States Patent [19]

Thompson et al.

[11] 4,140,648
[45] Feb. 20, 1979

[54] AEROSOL FOAMS

[76] Inventors: John Thompson, Maidenhead; Adrian Pitfield, High Wycombe, both of England

[21] Appl. No.: 662,282

[22] Filed: Feb. 27, 1976

[30] Foreign Application Priority Data

Feb. 27, 1975 [GB] United Kingdom ................ 8249/75

[51] Int. Cl.$^2$ ............................................. C11D 17/00
[52] U.S. Cl. ...................................... 252/90; 252/305; 252/307; 252/DIG. 7; 252/DIG. 13; 252/DIG. 14; 424/73
[58] Field of Search ......... 252/90, 305, 307, DIG. 13, 252/DIG. 14, DIG. 7; 424/73

[56] References Cited

U.S. PATENT DOCUMENTS

| 3,705,855 | 12/1972 | Marscher | 252/90 |
| 3,715,942 | 2/1973 | Courtney | 424/73 X |
| 3,719,752 | 3/1973 | Taylor | 252/305 X |
| 3,959,160 | 5/1976 | Horsler et al. | 252/90 |

Primary Examiner—Mayer Weinblatt

[57] ABSTRACT

Aerosol shaving foam formulations are provided containing as the foam forming medium an aqueous concentrate containing a selected nitrogen-containing surfactant and a long chain alcohol. An optional third surfactant, e.g. a nonionic surfactant, may be present.

6 Claims, No Drawings

AEROSOL FOAMS

FIELD OF INVENTION

This invention relates to pressurised shaving foam dispensers of the so-called aerosol type, and more particularly to the formulation of the foamable compositions used therein.

BACKGROUND OF INVENTION

In pressurised shaving foam dispensers of the above-mentioned type, a foamable concentrate, generally an aqueous soap solution, is contained in a dispenser equipped with a dispensing head and valve, and pressurised with a normally gaseous propellant, e.g. a low molecular weight hydrocarbon or hydrocarbon mixture, or a halohydrocarbon or halohydrocarbon mixture. In the container the liquefied propellant forms an emulsion in the foamable concentrate, the emulsion being referred to as an aerosol emulsion. Upon discharge of the emulsion through the dispensing head the volatilization of the dispersed liquid droplets of propellant causes the dispensed concentrate to foam. Depending upon the precise formulation of the concentrate, the dispensed product may range from a dense creamy foam to a light lather.

For the avoidance of doubt, the term "emulsion" will be used throughout this specification to refer to the whole liquid contents of the dispenser, i.e. the foamable concentrate plus liquid phase propellant, and the term "concentrate" will be used to refer to the liquid content of the dispenser, other than the propellant, "liquid" in this context embracing solutions, emulsions and suspensions. In other words, the concentrate itself may be an emulsion or suspension and not necessarily a solution of the foam producing ingredients in a suitable liquid medium, which in the case of the present invention will be water.

Various disclosures have been made of compositions suitable for use in such dispensers, amongst which may be mentioned U.K. Patent Specification No. 838,913 and U.S. Pat. No. 2,655,480. In accordance with the proposals of U.K. Patent Specification No. 838,913 aqueous soap solutions are used in which the quantity of alkali metal ammonium or alkylamine soaps, or soaps of primary or secondary alkanolamines, is kept below 4%, based on the weight of the concentrate, and in which the amount of triethanolamine soap is kept in minor proportion relative to the total soap content. In accordance with U.S. Pat. No. 2,655,480 aqueous soap solutions are also used, the actual concentration varying with the particular soap used. Thus, when triethanolamine stearate is used the concentration may be from 2–30% by weight of the solution and when potassium stearate is used the recommended amount is from 5 to 20%. A generally recommended range for all soap is 5 to 18%.

Yet other aqueous soap solutions are disclosed in U.S. Pat. No. 2,908,650, these being aqueous solutions of alkali metal soaps and soaps of nitrogen bases in specified proportions.

In such prior compositions a variety of additives have been proposed or used to modify or control the properties of the foam or emulsion. For example, U.S. Pat. No. 2,655,480 discloses that water-soluble non-ionic or anionic wetting agents may be added in amounts up to 5 or 6%, based on the weight of the concentrate, to facilitate rinsing of the lather from the face and avoiding oily deposits on the skin. Particular anionic and non-ionic wetting agents mentioned are sodium lauryl sulphate, sodium dodecyl benzene sulphonate, and water-soluble polyoxyethylene ethers of alkyl-substituted phenols. In addition, glycerine may also be added to stabilize the lather. U.K. Patent Specification No. 838,913 discloses the addition of small amounts (1–3%) of water-soluble emulsifiers, e.g. fatty acid alkanolamides. U.K. Pat. No. 838,913 also discloses the addition of water-insoluble fatty acids, fatty alcohols and their ethylene oxide derivatives, to give the lather a creamy character and effect a slight fatting of the skin. In addition, U.K. Pat. No. 838,913 further teaches the addition of relatively high amounts (up to 15%) of water-insoluble free fatty acid to effect stabilization of the lather.

Reference may also be made to the studies reported in J. Soc. Cosmetic Chemists, 17 (1966), pages 801–830 on the effects of the addition of long chain fatty alcohols to aqueous aerosol emulsions based on anionic surfactants, in particular on certain triethanolamine soaps and on sodium lauryl sulphate. In general, the addition of long chain alcohols to these emulsions showed an increase in viscosity and emulsion stability, judged on the time required for phase separation after shaking the aerosal container by hand. Increases were also noted in foam stability and foam stiffness.

Although soap-based aerosol shaving foams have attained a certain degree of popularity, the formulations currently used have certain disadvantages, the foremost of which is the tendency, when used, to form a scum either in the form of hardwater deposits, particularly, of course, when used in hard water areas, or in the form of free fatty acid. This scum, in turn, forms unsightly deposits around the wash basin and, more particularly, on the razor and because of the difficulty of removing these deposits, which are often not removed by simple rinsing, the razor rapidly becomes encrusted.

Soapless aerosal foams based on synthetic surfactants and containing a synthetic surfactant in combination with a long chain fatty acid or alcohol have been described. For example, in Soap and Chemical Specialities, July 1967, pages 70–78 and 162, continued in Soap and Chemical Specialities, August 1967, pages 70–74, 104 and 106, and in J. Soc. Cosmetic Chemists 20, (August 1969) 577–593, Sanders describes a series of studies on aerosol emulsion systems based on certain polyethylene fatty ethers in combination with certain long chain fatty acids and alcohols. Again, increases in emulsion viscosity and stability and increases in foam stability and stiffness were noted. Whilst, since such systems are soap free, the problem of hard water scum does not arise, it has been found that such systems have a particular disadvantage in that they lack storage stability, particularly at moderately elevated temperatures, e.g. 30°–40° C., which in practice may well occur when the products are stored or placed on display, for example, in a shop window exposed to bright sunlight or are used in a hot climate. Under these exposed conditions, compositions containing a synthetic surfactant solution and a long chain fatty alcohol or acid, as described in these articles, undergo an irreversible phase separation, that is to say they cannot be redispersed merely by shaking the aerosol container by hand, with the result that the emulsion no longer foams, or foams inadequately upon discharge from the container. Such products therefore lack the necessary shelf-life. In addition, separated solid phase material may block the valve and discharge apertures and thus further contribute to the malfunction of the container.

In our U.K. Patent Specification No. 1,423,179 and the corresponding German application published as OLS No. P 24 22 937.6 there are disclosed aerosol shaving foam preparations comprising a particular combination of surfactant materials, such preparations having the advantageous properties of not only being free from scum formation when used in hard water, but also having the ability to disperse preformed scums, which result, for example, when the face is washed with ordinary soap under hard water conditions prior to shaving. Furthermore, these preparations are stable at moderately elevated temperatures, e.g. 30°–40° C., for long periods. Broadly speaking, such preparations are based on an aerosol emulsion containing as the surfactant a combination, in particular proportions, of (i) a water-soluble nonionic, anionic or weakly cationic synthetic surfactant, (ii) a water-insoluble long chain fatty alcohol and (iii) an anionic surfactant which is either an alkali metal or alkanolamine soap or an alkyl or alkaryl sulphate, sulphonate or ether sulphate, or an N-acyl sarcosinate. Such compositions therefore contain as essential components two different types of surfactant, both of which are water-soluble or substantially water-soluble (i.e. self dispersing) and a third insoluble ingredient namely the long chain fatty alcohol. Preferably the water-soluble synthetic surfactant, component (i), is a nonionic surfactant, e.g. an ethylene oxide adduct of a long chain fatty alcohol, which is used in combination with myristyl alcohol and an alkali metal or alkanolamine soap.

However, other water-soluble surfactants may be used in such compositions, as component (i) including various nitrogen containing nonionic and anionic surfactants, such as long chain fatty acid amides, N-acyl-N-alkyl taurates, long chain N-acyl sarcosinates, long chain alkyl and alkaryl amine oxides, and ethylene and propylene oxide adducts of long chain fatty amines. Where an anionic surfactant is used as component (i), then it is of necessity other than an anionic surfactant already specified under component (iii). Water-soluble amphoteric surfactants may also be used e.g. long chain alkylamino acids, betaines, sulphobetaines, and imidazolines.

OBJECTS OF THIS INVENTION

The object of this invention is to provide stable aerosol foam emulsions having good foam forming properties and which are entirely soap-free. This is in contrast to the compositions disclosed in the aforesaid U.K. Patent Specification and German OLS, in which the compositions do preferably contain a soap, albeit in reduced amount. A further object is to provide stable aerosol foam emulsions having good foaming properties and which are scum-free and have scum-dispersing properties when used in hard water.

SUMMARY OF INVENTION

In accordance with this invention we have discovered that certain selected nitrogen-containing surfactants, namely water-soluble ethylene oxide adducts of long chain alkylamines and long chain fatty acid monoamides, water-soluble long chain alkylamine oxides, water-soluble imidazolines containing a $C_{12-14}$ alkyl substituent and water-soluble long chain alkyl group containing betaines, when used in combination with a water-insoluble long chain fatty alcohol, particularly tetradecanol (myristyl alcohol), give rise to aerosol emulsions of considerable stability even at the moderately elevated temperatures referred to above without requiring any other surfactant component as a stabiliser; that is to say stable emulsions are obtained with a two component system, as opposed to the three component systems disclosed in OLS No. P 24 22 937.6. In this connection, it should be mentioned that the term "stability" is being used in a somewhat wider sense than that which is normally associated with the phrase "a stable emulsion." Where used in this specification in relation to emulsions, "stable" is to be taken to include not only cases where there is little or no phase separation on standing, but also cases where there may be phase separation when the emulsion is left to stand for any length of time provided that the emulsion can easily be re-established by a few shakes of the hand.

DETAILED DESCRIPTION

In accordance with the present invention, there is provided an aerosol foam dispenser comprising a pressurised container equipped with a dispensing head and manually operable valve, and containing therein an aqueous soap-free surfactant concentrate, and emulsified or readily emulsifiable therewith, a normally gaseous aerosol propellant in liquid phase, said concentrate consisting essentially of water and (i) from 1–15% by weight of the concentrate, preferably 4–10%, of a water-soluble nitrogen-containing surfactant selected from ethylene oxide adducts of long chain alkylamines, being adducts of the formula:

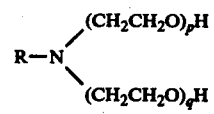

where R is a straight chain $C_{12}$–$C_{18}$ alkyl group and $p$ and $q$ are both positive integers of from 1–30 and totalling from 10–30; ethylene oxide adducts of long chain fatty acid monoamides, being adducts of the formula

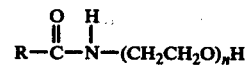

where R is a straight chain $C_{12}$–$C_{18}$ alkyl group and $n$ is an integer of from 3–9; an imidazoline of the formula:

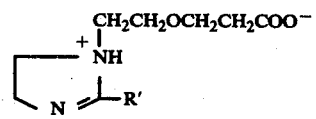

where R' is a straight chain $C_{12}$–$C_{14}$ alkyl group; long chain alkylamine oxides of the formula:

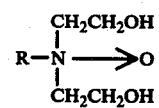

where R is a straight chain $C_{12}$–$C_{18}$ alkyl group; and long chain alkyl group containing betaines of the formula:

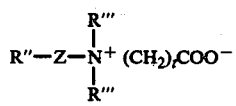

where R'' is a straight chain $C_{11}$–$C_{17}$ alkyl group, each R''' is a $C_1$–$C_3$ alkyl group, Z is a —$CH_2$— or —$CH_2CONH(CH_2)_x$— group, where x is an integer of from 2–5, and t is an integer of from 2–5, (ii) from 0.5–6% by weight of the concentrate, preferably 1–3%, of a water-insoluble long chain fatty alcohol, preferably tetradecanol;

the combined HLB value of the components (i) and (ii) in said concentrate being in the range 8–18 and the weight ratio of said nitrogen-containing surfactant to long chain fatty alcohol being in the range 0.5:1 to 12:1, preferably 2:1 to 6:1.

Although not essential, the above-described two component systems may contain up to 15% by weight, e.g. from 3–8%, of one or more other surfactants compatible with the nitrogen-containing surfactant and being other than water-soluble anionic surfactants selected from alkali metal and alkanolamine soaps, long-chain alkyl or alkaryl sulphates, sulphonates or ether sulphates or N-acyl sarcosinates. Such additional surfactants may be added to improve the emulsion stability still further, to facilitate re-emulsification of the system after standing and/or to vary the properties, e.g. stiffness, of the foam. By compatible we mean capable of existing in admixture in aqueous dispersion or solution with the other surfactant components of the system without precipitation or loss of surface activity. Thus where used, the additional surfactant may be anionic, nonionic, amphoteric or weakly cationic in character. Where used, the additional surfactant will be such that the HLB value of the total surfactant component (including the fatty alcohol) of the concentrate will be in the range 8–18 and the weight ratio of nitrogen-containing surfactant and additional surfactant to long-chain alcohol is in the range 0.5:1 to 12:1.

Typical additional surfactant components which may be used in the present invention are nonionics such as alkylene oxide (e.g. ethylene and/or propylene oxide) adducts of long chain fatty alcohols and acids, and of polyol esters of long chain fatty acids, and of $C_5$–$C_{12}$ alkyl phenols; and polyol (e.g. sucrose) esters of long chain fatty acids. Particular mention may be made of polyoxyethylene adducts of $C_{12}$–$C_{18}$ alcohols containing from 10–30 ethylene oxide units, nonyl phenoxypolyoxyethylene (50) ethanol and polyoxyethylene (20) sorbitan monostearate.

Throughout this specification the expression "long chain" when used in expressions such as "long chain fatty acids," "long chain fatty alcohol", "long chain alkyl" is intended to cover straight chain groups containing from 12–18 carbon atoms, whilst the expression "long chain alkaryl" is intended to cover alkyl-substituted aryl groups comprising a benzene or naphthalene nucleus substituted by a straight chain $C_5$–$C_{12}$ alkyl substituent. It is also to be understood that, as is customary in referring to surfactants, phrases specifying a carbon atom range, e.g. $C_{12}$–$C_{18}$, or a specific number of carbon atoms, e.g. $C_{12}$ alkyl, when referring to a surfactant component are intended to cover mixtures of compounds in which the alkyl substituents are predominantly within the stated range, or are predominantly alkyl groups having that particular number of carbon atoms, but which may contain small amounts of other compounds in which the alkyl groups are outside the stated range or which may contain unsaturated, e.g. alkenyl, groups, the reason being, of course, that in practice, such surfactants are frequently obtained from natural products, e.g. coconut oil, which are themselves mixtures of compounds of different chain lengths, but with one or a small range of chain lengths predominating.

The water-soluble nitrogen-containing surfactants used in this invention are all commercially available materials. Typical nitrogen-containing surfactants useful in this invention are condensates of long chain amines such as coco amine or tallow amine with up to 30 moles of ethylene oxide, bis-(2-hydroxyethyl) substituted N-oxides of coco amine and tallow amine, condensates of long chain fatty acid amides, e.g. tallow amide, with from 4–9 moles of ethylene oxide, and coco and tallow substituted betaines and imidazolines. Specific nitrogen-containing surfactants useful in this invention are:

Polyoxyethylene (15) tallow amine
Polyoxyethylene (15) coco amine
Bis-(2-hydroxyethyl) tallow amine oxide
2-coco-1-(ethyl-β-oxipropanoic acid)imidazoline
Polyoxyethylene (8) tallow monoethanolamide
Coco-amidopropyl dimethylaminoacetic acid betaine.

Where, in any of the compositions according to this invention the imidazoline or betaine is used as the nitrogen-containing surfactant, it may be used in anionic, isoelectric or cationic form. Preferably, it is used in anionic form and the pH of the concentrate is adjusted to a value in the range 8–9.5 with a suitable base e.g. triethanolamine, sodium hydroxide or potassium hydroxide.

Generally speaking the total solids concentration of the aqueous concentrates used in the present invention will be from 5–30% by weight, preferably 8–20% by weight, based on the weight of the concentrate, but these amounts are not critical.

The propellants employed in the compositions used in the present invention are conventional materials, e.g. hydrocarbon and hydrocarbon mixtures, e.g. the mixture of butane, isobutane and propane known commercially as Butane 40, and halohydrocarbons such as dichlorodifluoromethane (12) on its own or mixtures thereof with dichlorotetrafluoroethane (114). Mixtures of hydrocarbon and halohydrocarbon propellants may also be used. The quantity of propellant used will generally be in the range 3–12% by weight of the total emulsion, depending on the propellant used, although the exact amount is by no means critical to this invention. Generally speaking, hydrocarbon propellants such as butane mixtures will be used in amounts at the lower end of the stated range, e.g. 3–7%, whilst halohydrocarbon propellants will be used in amounts at the upper end of the range, e.g. 7–12%. Generally preferred as propellants will be the halohydrocarbons, particularly fluorocarbons, and mixtures thereof with hydrocarbons. Hydrocarbon propellants on their own are less preferred.

Other ingredients such as antioxidants, perfuming agents, stabilizers, viscosity modifiers, humectants, emollients and lubricants, may be included in the compositions of this invention in minor amounts as is conventional in the art, and are embraced by the phrase "consisting essentially of."

Examples of aerosol shaving foam preparations according to the invention are as follows. Each composition was packaged in a conventional pressurised dispenser equipped with conventional discharge valve and foam dispensing head. In every case, a good stiff foam could be dispensed from the nozzle after shaking the dispenser in the hand for a few seconds before opening the valve. This ability was maintained even after the packages had been allowed to stand for prolonged periods of time at temperatures up to 40° C.

Typical foamable aerosol emulsions according to this invention are illustrated in Examples 1-11.

EXAMPLE 1

|  | Wt.% |
|---|---|
| Polyoxyethylene (15) tallow amine | 4.11 |
| Myristyl alcohol | 2.02 |
| Distilled water | 85.47 |
| Propellant 12/114 (60:40) | 8.40 |

EXAMPLE 2

|  | Wt.% |
|---|---|
| 2-Coco-1-(ethyl-β-oxiporopanoic acid) imidazoline | 4.58 |
| Triethanolamine | 1.61 |
| Myristyl alcohol | 2.02 |
| Distilled water | 83.39 |
| Propellant 12/114 (60:40) | 8.40 |

EXAMPLE 3

|  | Wt.% |
|---|---|
| Polyoxyethylene (15) coco amine | 3.87 |
| Myristyl alcohol | 2.02 |
| Sorbitol | 2.00 |
| Distilled water | 83.71 |
| Propellant 12/114 (60:40) | 8.40 |

EXAMPLE 4

|  | Wt.% |
|---|---|
| Bis (2-hydroxyethyl) tallow amine oxide | 3.79 |
| Myristyl alcohol | 2.02 |
| Glycerol | 5.00 |
| Distilled water | 80.79 |
| Propellant 12/114 (60:40) | 8.40 |

EXAMPLE 5

|  | Wt.% |
|---|---|
| Polyoxyethylene (8) tallow monoamide | 4.58 |
| Myristyl alcohol | 1.83 |
| Distilled water | 85.19 |
| Propellant 12/114 (60:40) | 8.40 |

EXAMPLE 6

|  | Wt.% |
|---|---|
| Bis (2-hydroxyethyl) tallow amine oxide | 3.66 |
| Myristyl alcohol | 1.97 |
| Sorbitan monolaurate | 1.60 |
| Distilled water | 84.37 |
| Propellant 12/114 (60:40) | 8.40 |

EXAMPLE 7

|  | Wt.% |
|---|---|
| Fatty ($C_{11}$–$C_{17}$) amidopropyl dimethylaminoacetic acid betaine | 4.58 |
| Myristyl alcohol | 2.02 |
| Polyacrylic acid (mol. wt. 76,000) | 1.83 |
| Triethanolamine | 0.92 |
| Distilled water | 82.25 |
| Propellant 12/114 (60:40) | 8.40 |

EXAMPLE 8

|  | Wt.% |
|---|---|
| Fatty ($C_{11}$–$C_{17}$) amidopropyl dimethylaminoacetic acid betaine | 4.58 |
| Myristyl alcohol | 2.75 |
| Polyoxyethylene (20) sorbitan monostearate | 4.58 |
| Triethanolamine | 0.92 |
| Distilled water | 78.77 |
| Propellant 12/114 (60:40) | 8.40 |

EXAMPLE 9

|  | Wt.% |
|---|---|
| 2-Coco-1-(ethyl-β-oxipropanoic acid) imidazoline | 4.58 |
| Triethanolamine | 0.92 |
| Myristyl alcohol | 1.83 |
| Polyoxyethylene (20) cetyl ether | 4.58 |
| Distilled water | 79.69 |
| Propellant 12/114 (60:40) | 8.40 |

EXAMPLE 10

|  | Wt.% |
|---|---|
| Polyoxyethylene (4) coco monoamide | 5.50 |
| Polyoxyethylene (20) cetyl ether | 4.58 |
| Myristyl alcohol | 2.02 |
| Distilled water | 79.50 |
| Propellant 12/114 (60:40) | 8.40 |

EXAMPLE 11

|  | Wt.% |
|---|---|
| Polyoxyethylene (15) coco amine | 8.90 |
| Myristyl alcohol | 2.15 |
| Polyethylene glycol (mol. wt 400) monostearate | 1.90 |
| Distilled water | 78.65 |
| Propellant 12/114 (60:40) | 8.40 |

We claim:

1. An aerosol shaving foam dispenser containing therein an aqueous soap-free surfactant concentrate, and emulsified or readily emulsifiable therewith, a gaseous aerosol propellant in liquid phase, said concentrate consisting essentially of water and
(i) from 1–15% of a nitrogen-containing surfactant selected from the group consisting of:

$$R-N\begin{cases}(CH_2CH_2O)_pH \\ (CH_2CH_2O)_qH\end{cases}$$

where R is a straight chain $C_{12}$–$C_{18}$ alkyl group and p and q are both positive integers of from 1–30 and totalling from 10–30;

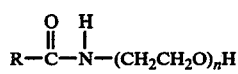

wherein R is a straight chain $C_{12}$–$C_{18}$ alkyl group and n is an integer of from 3–9;

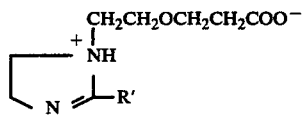

where R' is a straight chain $C_{12}$–$C_{14}$ alkyl group;

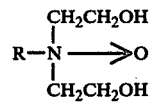

where R is a straight chain $C_{12}$–$C_{18}$ alkyl group; and

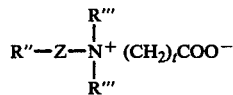

where R" is a straight chain $C_{11}$–$C_{17}$ alkyl group, each R'" is a $C_1$–$C_3$ alkyl group, Z is a —$CH_2$— or —$CH_2CONH(CH_2)_x$— group, where x is an integer of from 2–5, and t is an integer of from 2–5; and
(ii) from 0.5–6% by weight of the concentrate of a water-insoluble long chain fatty alcohol containing from 12–18 carbon atoms;
the combined HLB value of the components (i) and (ii) in said concentrate being in the range 8–18 and the weight ratio of said nitrogen-containing surfactant to long chain fatty alcohol being in the range 0.5:1 to 12:1.

2. A dispenser according to claim 1, wherein the long chain fatty alcohol is tetradecanol.

3. A dispenser according to claim 1, in which the aqueous surfactant concentrate contains from 4–10% of the nitrogen surfactant and from 1–3% of long chain alcohol, and the weight ratio of components (i) and (ii) is in the range 2:1 to 6:1.

4. A dispenser according to claim 3, wherein the long chain fatty alcohol is tetradecanol.

5. An aerosol foam dispenser containing therein an aqueous soap-free surfactant concentrate, and emulsified or readily emulsifiable therewith, a gaseous aerosol propellant in liquid phase, said concentrate consisting essentially of water and (i) from 1–15% by weight of the concentrate of a water-soluble nitrogen-containing surfactant selected from the group consisting of:

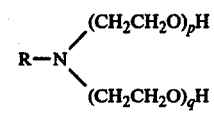

where R is a straight chain $C_{12}$–$C_{18}$ alkyl group and p and q are both positive integers of from 1–30 and totalling from 10–30;

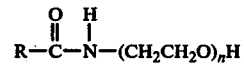

where R is a straight chain $C_{12}$–$C_{18}$ alkyl group and n is an integer of from 3–9;

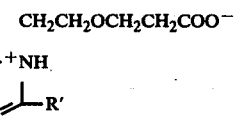

where R' is a straight chain $C_{12}$–$C_{14}$ alkyl group;

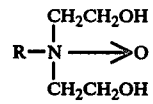

where R is a straight chain $C_{12}$–$C_{18}$ alkyl group; and

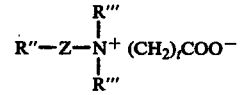

where R" is a straight chain $C_{11}$–$C_{17}$ alkyl group, each R'" is a $C_1$–$C_3$ alkyl group, Z is a —$CH_2$— or —$CH_2CONH(CH)_x$— group, where x is an integer of from 2–5, and t is an integer of from 2–5;
(ii) from 0.5–6% by weight of the concentrate of a water-insoluble long chain fatty alcohol containing from 12–18 carbon atoms; and
(iii) up to 15% by weight of the concentrate of adducts of a $C_{12}$–$C_{18}$ fatty alcohol with 10–30 moles of ethylene oxide, nonyl phenoxypolyoxyethylene (50) ethanol, and polyoxyethylene (20) sorbitan monostearate, the HLB value of components (i), (ii) and (iii) being in the range 8–18 and the weight ratio of components (i) and (iii) to component (ii) being in the range 0.5:1 to 12:1.

6. A dispenser according to claim 5, wherein the long chain fatty alcohol is tetradecanol.

* * * * *